United States Patent [19]

Munnerlyn et al.

[11] 4,192,317

[45] Mar. 11, 1980

[54] INDENTATION TONOMETER

[75] Inventors: Charles R. Munnerlyn, Sunnyvale; Terrance N. Clapham, San Jose, both of Calif.

[73] Assignee: Ical, Incorporated, Sunnyvale, Calif.

[21] Appl. No.: 920,806

[22] Filed: Jun. 30, 1978

[51] Int. Cl.² .............................................. A61B 3/16
[52] U.S. Cl. ................................................... 128/646
[58] Field of Search .............. 128/2 T, 2 R, 646, 652, 128/645; 73/80; 356/374, 375

[56] References Cited

U.S. PATENT DOCUMENTS

| | | | |
|---|---|---|---|
| 3,062,042 | 11/1962 | Gulden | 73/80 |
| 3,070,087 | 12/1962 | Sittel | 128/2 T |
| 3,070,997 | 1/1963 | Papritz et al. | 73/80 |
| 3,266,301 | 8/1966 | Sovatkin | 73/80 |
| 3,564,907 | 2/1971 | Holcomb et al. | 128/2 T X |
| 3,724,263 | 4/1973 | Rose et al. | 73/80 |
| 3,796,498 | 3/1974 | Post | 356/374 |
| 3,992,926 | 11/1976 | Berryhill | 73/80 |
| 4,115,008 | 9/1978 | Shepherd | 356/374 |

FOREIGN PATENT DOCUMENTS 446681 7/1927 Fed. Rep. of Germany .............. 73/80

OTHER PUBLICATIONS

*Berkeley Bio-Engineering Pamphlet,* Electro-Medical Technology, Inc. pamphlet.

*Primary Examiner*—Kyle L. Howell
*Attorney, Agent, or Firm*—Stonebraker, Shepard & Stephens

[57] ABSTRACT

An indentation tonometer is contained within a hand holdable housing below which extends a foot plate and a movable plunger. An optical encoder is disposed within the housing and has a ruled scale that is fixed relative to the foot plate and an adjacent ruled scale that is movable relative to the fixed scale. The movable scale engages an upper surface of the plunger and is elevated to a position corresponding to the position of the plunger relative to the foot plate as intraocular pressure is measured. Components for the optical encoder are arranged within the housing to produce a digital readout. The foot plate and plunger are preferably arranged in a subassembly that is vertically movable relative to the housing with suitable switches arranged for detecting when a reading is completed and for automatically calibrating the instrument on the test block. The foot plate and pluger are readily removable, plungers are interchangeable, and the instrument preferably has a memory capable of storing the data from measurement of two eyes.

12 Claims, 4 Drawing Figures

INDENTATION TONOMETER

BACKGROUND OF THE INVENTION

Indentation tonometers of the Schiotz type have been known for years and have been developed in various ways. Much knowledge is available on the foot plate, the plunger, relative movements and measurement values, plunger weights, and other information. Indentation tonometers have also been made with transducers to transform the movement of the plunger relative to the foot plate into an electrical signal that is processed electronically to produce a digital display and to record values. Prior art indentation tonometers of the mechanical variety suffer from inaccuracies, operator error, and critical manufacturing tolerances; and prior art indentation tonometers of the electrical variety having a digital readout suffer from complexity, large size, expense, and inconvenient operation.

This invention involves recognition of the problems of prior art indentation tonometers and proposes a simple way of making an automatic, digital reading instrument that is small, convenient, accurate, inexpensive, and self-contained within a hand holdable housing. The invention also aims at reliability, compatibility with existing parameters in the indentation tonometry art, and ease of cleaning and adapting the instrument to different measurements.

SUMMARY OF THE INVENTION

The inventive indentation tonometer has a foot plate and a plunger movable relative to the foot plate and includes a housing that is hand holdable and manipulatable. The foot plate and plunger are supported to extend below the housing, and an optical encoder is disposed within the housing and has a ruled scale that is fixed relative to the foot plate and an adjacent ruled scale that is movable relative to the fixed scale. An upper surface of the plunger engages the movable scale for elevating the movable scale relative to the fixed scale to correspond to the position of the plunger relative to the foot plate as the intraocular pressure of an eye is measured. Components for the optical encoder including electric power supply, electric circuitry, and digital readout are all arranged in the housing for indicating a measure of the intraocular pressure derived from the position of the movable scale relative to the fixed scale. The foot plate is preferably releasably secured to the lower end of a cylinder containing the plunger; and the subassembly including the foot plate, plunger, and optical encoder is preferably movable vertically relative to the housing and operates switches for measurement and calibration purposes.

DRAWINGS

DETAILED DESCRIPTION

Figure 1:
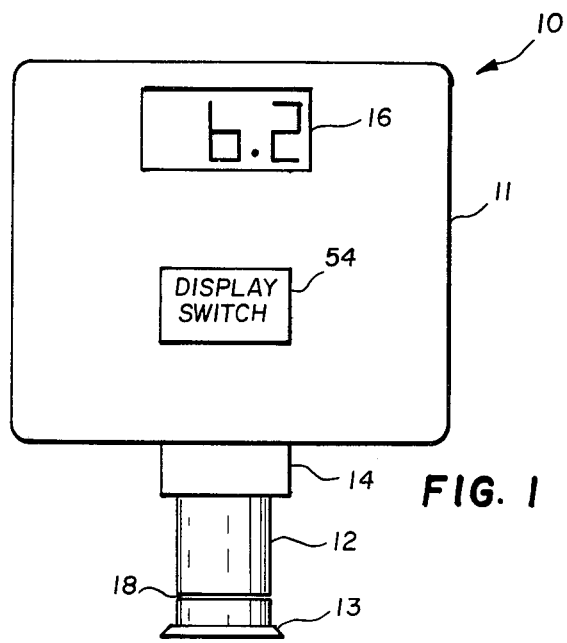
FIG. 1 is a front elevational view of a preferred embodiment of the inventive indentation tonometer.

Indentation tonometer 10 has a housing 11 that is hand holdable and manipulatable and below which extends a tube 12 bearing a foot plate 13 and containing a vertically movable plunger 15 for measuring the intraocular pressure of an eye as generally understood in the art of tonometry. Instrument 10 is used in the vertical position illustrated and is lowered to rest foot plate 13 against the cornea of an eye so that intraocular pressure can be measured and digitally displayed in display 16; and throughout the specification and claims, the usual vertical orientation of instrument 10 is assumed as its components and operation are described.

The tonometry art has established standards for indentation tonometers as to physical dimensions of foot plate 13 and plunger 15, weights, friction, conversion of indentation values to intraocular pressure values, and other relevant measurement parameters; and instrument 10 preferably conforms to such standards.

Figure 3:
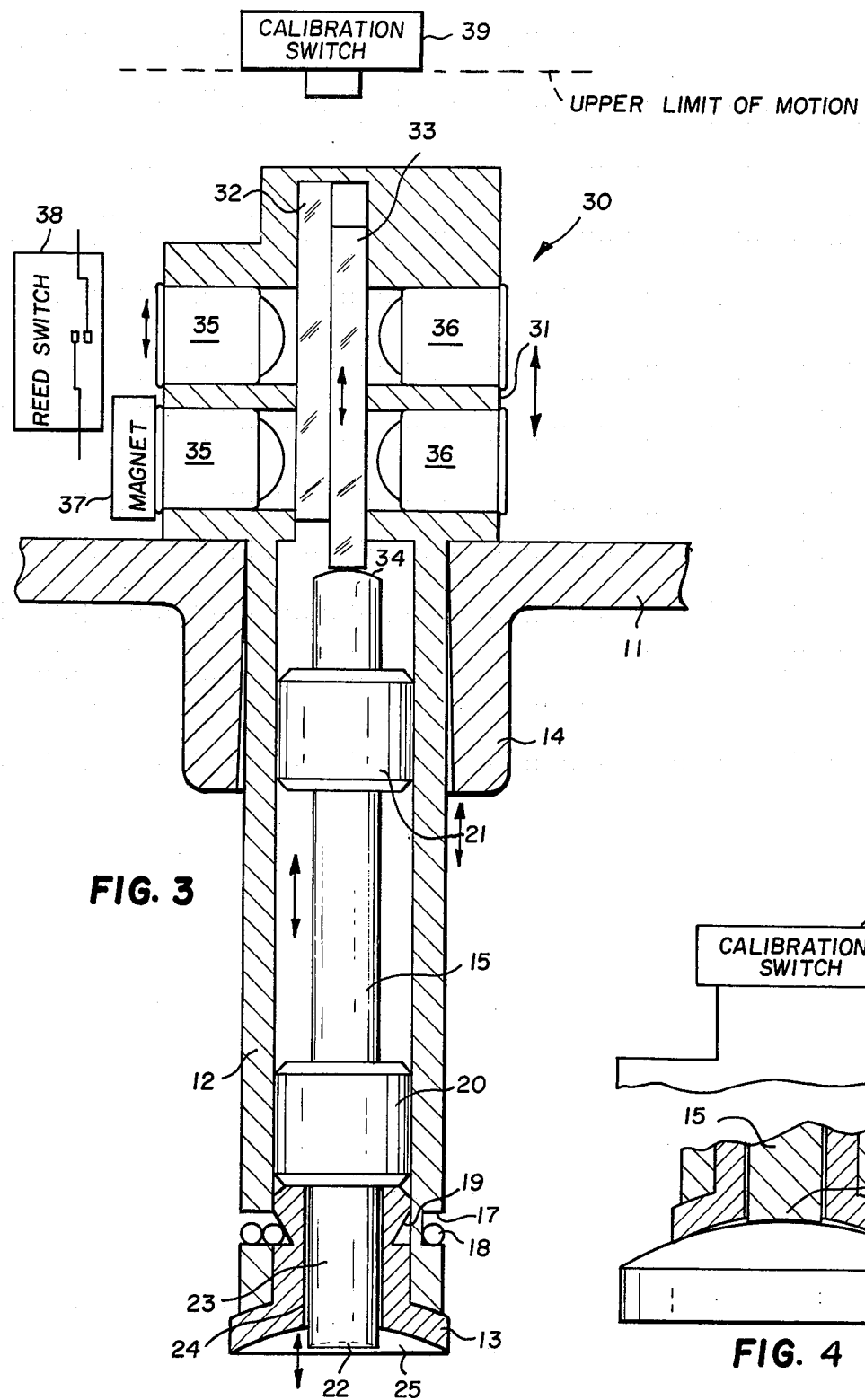
FIG. 3 is an enlarged cross-sectional view of the mechanically movable portions of the tonometer of FIGS. 1 and 2.

The mechanical functioning of tonometer 10 is best shown in FIG. 3. Tube or tube-shaped element 12 extends downward through a sleeve 14 formed on the underside of housing 11, and tube 12 is preferably tiltable in sleeve 14 for a few degrees in any direction off the vertical axis. The freedom of motion of tube 12 around the vertical axis by virtue of the tapered opening through sleeve 14 allows housing 11 to be held or moved slightly off the true vertical without forcing tube 12 and foot plate 13 to move relative to the eye. Such freedom of motion of tube 12 also aids in calibrating the instrument by pressing the foot plate and plunger against a test surface as described below.

Near the bottom of tube 12 is an annular groove 17 holding a spring clip 18, and groove 17 opens into the interior of tube 12 so that spring clip 18 can engage an annular notch 19 in foot plate 13 for releasably securing foot plate 13 to the bottom of tube 12 in a quick-release connection. Foot plate 13 has a snap fit in tube 12 and can be removed simply by being pulled downward, with spring clip 18 flexing enough to allow manual removal of foot plate 13. When foot plate 13 is removed, plunger 15 moves downward toward the open end of tube 12 but is retained from falling out of tube 12 by engagement with spring clip 18.

Plunger 15 is formed with a pair of bearing surfaces 20 and 21 that fit and guide in the inside of tube 12 so that plunger 15 can move vertically with very little friction in a smooth sliding fit within tube 12. Plunger 15 is prevented from falling out of the open end of tube 12 after removal of foot plate 13 by the snap fit engagement of spring clip 18 with the lower edge of bearing 20 on plunger 15. Plunger 15 can also be manually removed from tube 12 by pulling outward to overcome the resilient grip of spring clip 18. Easy removal of foot plate 13 and plunger 15 by a quick-release connection facilitates sterilization of parts and easy interchange of plungers which vary in weight according to known tonometry standards.

The lower stem 23 of plunger 15 has a loose fit in a central bore 24 in foot plate 13 so that tears rising in the space between plunger stem 23 and foot plate bore 24 do not create friction or affect the operation of the instrument. The lower end 22 of plunger 15 cooperates with the bottom concave surface 25 of foot plate 13 in a generally known way for measuring intraocular pressure.

Tube 12, foot plate 13, and plunger 15 are part of a subassembly secured to optical encoder 30 disposed within housing 11 as illustrated. A housing part 31 for optical encoder 30 is preferably formed integrally with tube 12. The subassembly including tube 12 and optical encoder 30 is movable vertically relative to housing 11 by a small amount such as 6 to 8 millimeters in part to accomplish switching operations described below.

Optical encoder 30 includes a ruled scale 32 that is fixed relative to foot plate 13, tube 12, and housing 31 to be movable with the subassembly. Adjacent scale 32 is a relatively movable ruled scale 33 capable of moving vertically a small distance within a slot as plunger 15 moves vertically relative to foot plate 13. Movable scale 33 rests gravitationally on the upper end 34 of plunger 15 for a direct and simple contact with plunger 15. Then as plunger 15 moves upward relative to foot plate 13 as intraocular pressure is measured, movable scale 33 directly moves upward relative to scale 32 by the same amount. The optical rulings on scales 32 and 33 produce moire fringes that are detected in generally known ways for measuring the movement of plunger 15 relative to foot plate 13. A pair of light-emitting diodes 35 directs light through scales 32 and 33, and the light passing through the rulings is detected by a pair of detectors 36; and the positioning of detectors 36 relative to the rulings on scales 32 and 33 is arranged so that both the direction and distance of relative motion between the scales can be readily determined.

A magnet 37 secured to housing 31 moves vertically as housing 31 moves relative to housing 11, and magnet 37 is positioned for operating reed switch 38. As housing 11 is moved downward relative to tube 12 and housing 31 in measuring an eye, magnet 37 moves upward relative to reed switch 38 which is fixed in housing 11. When housing 11 has moved down 3 to 4 millimeters relative to tube 12, which is far enough to insure that a reading is complete, magnet 37 moves upward sufficiently to actuate reed switch 38. This sounds an audible tone so that the operator can remove the instrument from the eye, and it also stores the measured result in an electronic memory and displays the reading in display window 16.

Figure 4:
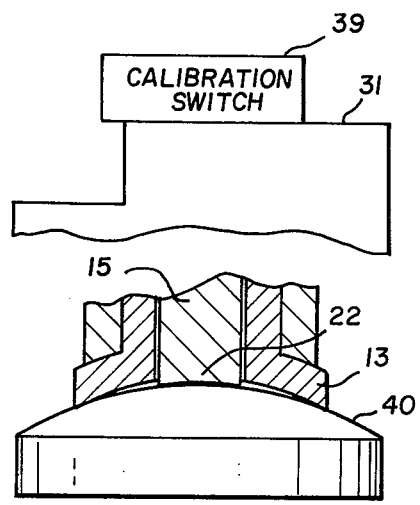
FIG. 4 is a fragmentary, cross-sectional view showing a preferred way of calibrating the tonometer of FIGS. 1–3.

Calibration switch 39 is arranged at the upper limit of motion of housing 31 relative to housing 11 for automatically calibrating the instrument. To do this, tonometer 10 is lowered onto a spherical test surface 40 so that foot plate 13 engages surface 40 and plunger 15 is forced upward relative to foot plate 13. Test surface 40 has a slightly larger radius than the underside of foot plate 13 so that plunger 15 assumes a zero position that is 0.05 millimeters below the zenith of the spherical locus of foot plate 13 as shown in FIG. 4 and as generally known in the tonometry art. This lifts tube 12 and housing 31 relative to housing 11 to move housing 31 6 to 8 millimeters upward to its upper limit of motion against calibration switch 39 which actuates to set the instrument circuitry for a zero position reading for plunger 15 relative to foot plate 13. Actuation of calibration switch 39 also sounds a continuous tone informing the operator that automatic calibration is completed. From the operator point of view, the instrument is merely gripped manually and pressed down as far as possible against test surface 40 until a steady tone is heard and calibration is automatically complete.

Figure 2:
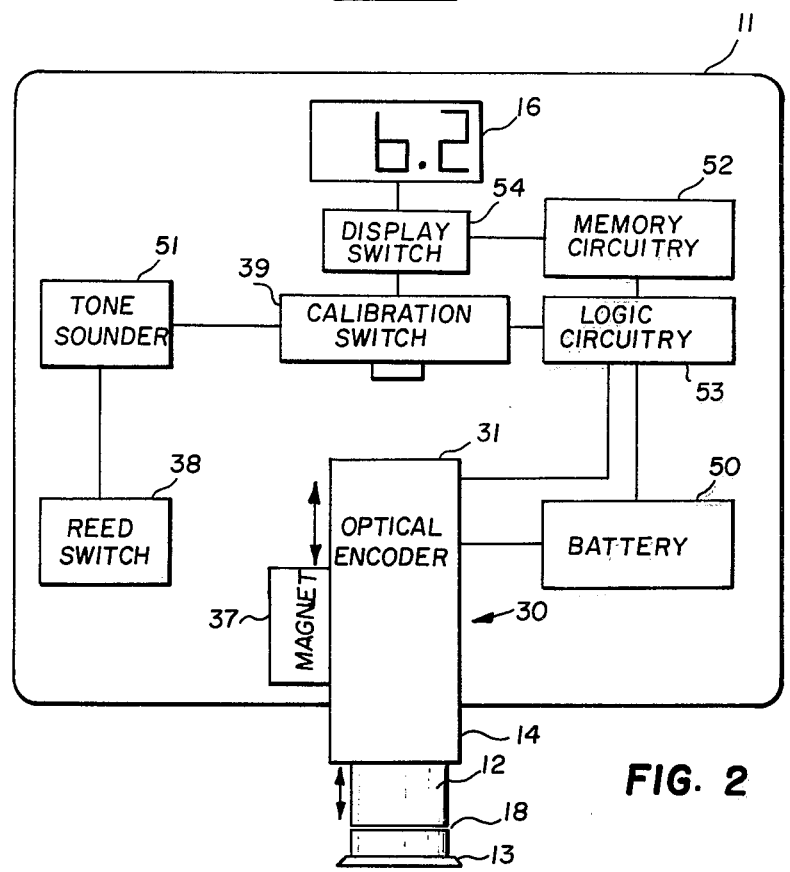
FIG. 2 is a schematic diagram of the tonometer of FIG. 1 showing the interaction of components.

As best shown in FIG. 2, housing 11 also contains a battery 50 providing a source of electric power to optical encoder 30 and other components. An audible tone sounder 51 is in communication with reed switch 38 and calibration switch 39 and preferably sounds a brief tone when reed switch 39 is closed to indicate completion of a measurement and a steady tone upon actuation of calibration switch 39 at the completion of an instrument calibration. Electronic circuitry for the instrument preferably includes memory circuitry 52 along with logic circuitry 53 and a display switch 54. The circuitry is arranged in cooperation with switch 54 for storing two eye readings in memory circuitry 52 and alternately displaying these readings in display 16 upon actuation of switch 54. This allows quick measurements of the intraocular pressure of both eyes of the patient with the instrument storing both readings which can be transcribed by using switch 54 after the measurements are completed.

Instrument 10 is preferably compact and self-contained as illustrated to be complete with power supply and circuitry necessary for displaying digital readings of intraocular pressure measurements derived from optical encoder 30 cooperating with plunger 15 and foot plate 13. Instrument 10 is also relatively lightweight and easily held and manipulated with one hand. It has no cords or connections to remote locations, although it can be provided with timing and memory circuitry so that it can transfer data to a recording device after its measurements are completed. It is also reliable and accurate in using an optical encoder directly contacting the plunger.

There are many ways that housing shapes and component configurations can be made to cooperate with mechanical movements in applying the invention to indentation tonometers, once the basic relationship between a vertically movable plunger and an optical encoder is appreciated. The illustrated preferred embodiment is recommended, however, for its many advantages in reliability, accuracy, and economy.

We claim:

1. An indentation tonometer having a foot plate and a plunger movable relative to said foot plate, said tonometer comprising:
   a. a housing that is hand holdable and manipulatable;
   b. means in said housing for supporting said foot plate to extend below said housing;
   c. an optical encoder disposed within said housing and having a ruled scale that is fixed relative to said foot plate and an adjacent ruled scale that is movable relative to said fixed scale;
   d. an upper surface of said plunger engaging said movable scale for elevating said movable scale relative to said fixed scale to correspond to the position of said plunger relative to said foot plate as the intraocular pressure of an eye is measured; and
   e. components for said optical encoder including electric power supply, electric circuitry, and digital readout all being arranged in said housing for digitally indicating a measure of said intraocular pressure derived from the position of said movable scale relative to said fixed scale.

2. The tonometer of claim 1 wherein said movable scale rests gravitationally on said upper surface of said plunger.

3. The tonometer of claim 1 wherein a cylindrical tube extends downward from said housing, and said foot plate has a quick-release connection to a lower region of said tube.

4. The tonometer of claim 3 wherein said quick-release connection provides a snap fit retaining said foot plate in said lower region of said tube and also retains said plunger in said tube after removal of said foot plate from said tube.

5. The tonometer of claim 4 wherein said lower region of said tube has an opening, and a spring clip is arranged for extending resiliently into said opening for releasably securing said foot plate to said tube and for releasably retaining said plunger in said tube after removal of said foot plate from said tube.

6. The tonometer of claim 3 wherein said tube, said foot plate, and said optical encoder are supported for moving together vertically relative to said housing.

7. The tonometer of claim 6 wherein said tube is freely movable slightly off a vertical axis relative to said housing.

8. The tonometer of claim 6 wherein a magnet moves vertically with said tube, said foot plate, and said optical encoder; and an electric switch mounted in said housing is actuated by said magnet reaching a predetermined elevation relative to said housing to indicate completion of said measure of said intraocular pressure.

9. The tonometer of claim 8 including means for sounding a tone in response to actuation of said switch.

10. The tonometer of claim 6 wherein said movable scale rests gravitationally on said upper surface of said plunger.

11. The tonometer of claim 6 wherein a calibration switch is mounted in said housing for actuation at an upper limit of motion of said tube, said foot plate, and said optical encoder relative to said housing for automatically calibrating said tonometer to a zero position of said plunger relative to said foot plate as said foot plate and said plunger are pressed against a spherical test surface.

12. The tonometer of claim 11 including means for sounding a tone in response to actuation of said calibration switch.

* * * * *